United States Patent
Burke et al.

(10) Patent No.: US 10,755,368 B2
(45) Date of Patent: Aug. 25, 2020

(54) MEDICAL EQUIPMENT CUSTOMER WEB PORTAL

(71) Applicants: Edward Burke, Waltham, MA (US); Susan Claire Hopkins, Half Moon Bay, CA (US); Christopher Davis Parker, Danville, CA (US); James Renteria, Fremont, CA (US); Edward Lewis Rieflin, Mount Pleasant, SC (US); Gilbert Rivas, Danville, CA (US)

(72) Inventors: Edward Burke, Waltham, MA (US); Susan Claire Hopkins, Half Moon Bay, CA (US); Christopher Davis Parker, Danville, CA (US); James Renteria, Fremont, CA (US); Edward Lewis Rieflin, Mount Pleasant, SC (US); Gilbert Rivas, Danville, CA (US)

(73) Assignee: TC1 LLC, St. Paul, MN (US)

( * ) Notice: Subject to any disclaimer, the term of this patent is extended or adjusted under 35 U.S.C. 154(b) by 1133 days.

(21) Appl. No.: 13/826,063

(22) Filed: Mar. 14, 2013

(65) Prior Publication Data

US 2013/0253952 A1     Sep. 26, 2013

Related U.S. Application Data

(60) Provisional application No. 61/615,781, filed on Mar. 26, 2012.

(51) Int. Cl.
*G06Q 50/22* (2018.01)
*G06Q 10/00* (2012.01)
*G06F 19/00* (2018.01)

(52) U.S. Cl.
CPC ......... *G06Q 50/22* (2013.01); *G06F 19/3418* (2013.01); *G06Q 10/20* (2013.01)

(58) Field of Classification Search
CPC ........ G06Q 10/00; G06Q 50/00; G06Q 50/22; G06Q 10/20; G16H 10/00; G16H 10/40;
(Continued)

(56) References Cited

U.S. PATENT DOCUMENTS 7,048,185 B2     5/2006  Hart
8,346,632 B2 *   1/2013  Saghbini .................... 705/28
(Continued)

OTHER PUBLICATIONS

International Search Report and Written Opinion of the International Searching Authority for corresponding International Application No. PCT/US2013/033680, dated Sep. 11, 2013, 10 pages.
(Continued)

*Primary Examiner* — Robert W Morgan
*Assistant Examiner* — Charles P Coleman
(74) *Attorney, Agent, or Firm* — Womble Bond Dickinson (US) LLP

(57) ABSTRACT

A system for managing medical equipment is described. The system includes an equipment tracking module to maintain equipment records corresponding to medical equipment that are shipped from a medical equipment manufacturer to a medical center. The system also includes a patient information tracking module to maintain patient records corresponding to patients of the medical center and to associate the patient records with the equipment records when the patients are equipped with the medical equipment. In addition, the system includes a mapping module to provide locations of medical facilities capable of providing support for the medical equipment for patients that have been discharged from the medical center. Other embodiments are also described.

36 Claims, 6 Drawing Sheets

(58) Field of Classification Search
CPC ........ G16H 15/00; G16H 20/00; G16H 20/10; G16H 20/13; G16H 20/17; G16H 30/00; G16H 40/00; G16H 50/00; G16H 70/00; G16H 80/00; G06F 19/3418
USPC .................................................. 705/2, 3, 20
See application file for complete search history.

(56) References Cited

U.S. PATENT DOCUMENTS

| | | | |
|---|---|---|---|
| 8,428,966 B2 | 4/2013 | Green, III et al. | |
| 2001/0037220 A1* | 11/2001 | Merry et al. | 705/3 |
| 2003/0074223 A1* | 4/2003 | Hickle | A61J 1/14 705/2 |
| 2003/0114948 A1* | 6/2003 | Hellemann | G06Q 10/06 700/100 |
| 2005/0201345 A1 | 9/2005 | Williamson | |
| 2006/0168043 A1 | 7/2006 | Eisenberger et al. | |
| 2009/0024584 A1* | 1/2009 | Dharap | G06F 15/177 |
| 2010/0274591 A1* | 10/2010 | Wells | 705/3 |
| 2011/0057037 A1 | 3/2011 | Frysz et al. | |
| 2011/0270632 A1 | 11/2011 | Manning et al. | |
| 2011/0307274 A1* | 12/2011 | Thompson et al. | 705/3 |
| 2012/0016691 A1* | 1/2012 | Sievenpiper et al. | 705/2 |
| 2012/0116803 A1* | 5/2012 | Reid et al. | 705/2 |

OTHER PUBLICATIONS

OTTR, Chronic Care Solutions: May 24, 2013, http://www.ottr.com/solutions/ottrvad/ (4 pages).
OTTR: Solid Organ Transplant, May 24, 2013, http://www.ottr.corn/solutions/ottr/ (2 pages).
PRWeb, "TeleResults and Partners Build Ties at Fifth User Conference," Johns Hopkins University Hospital on Mar. 18 and 19, 2013, http://www.prweb.com/releases/teleresults/201303/prweb10561817.htm. (3 pages).
TeleResults,"Presidio VAD," Mar. 2013, http://www.prweb.com/releases/teleresults/201303/prweb10561817.htm. (2 pages).
International Preliminary Report on Patentability for corresponding International Application No. PCT/US2013/033680, dated Oct. 9, 2014 (8 pages).

* cited by examiner

MEDICAL EQUIPMENT CUSTOMER WEB PORTAL

CROSS-REFERENCE

This present application claims the benefit of U.S. Provisional Application Ser. No. 61/615,781, filed on Mar. 26, 2012, and this provisional application is hereby incorporated herein by reference.

FIELD

Embodiments of the invention relate to an Internet web portal; and more specifically, to methods and apparatus for providing and maintaining a web portal for customers and patients of medical equipment

BACKGROUND

Medical equipment manufacturers typically have internal resource planning systems (RPS) to manage the sales and shipments of medical equipment that the manufacturers sell. However, once the medical equipment is shipped from the manufacturer and reaches the customer (e.g., a medical center), it has been the customer's responsibilities to implement a system to maintain their own records related to the medical equipment and their patients, and to implement a system to manage their own inventory. Customers have traditionally used paper and electronic spreadsheets to keep track of the medical equipment and their patients. Some medical equipment such as implantable medical devices (e.g., implantable heart pumps) may be retained by a patient for many years. As the number of new patients and ongoing patients grow, managing the paper and electronic spreadsheets to keep track of the medical equipment and their patients becomes a cumbersome task for clinicians. It is also difficult to accurately track, fulfill, and report equipment maintenance on required schedules. Furthermore, when product incidents occur, the logistics of returning the medical equipment to the manufacturer for evaluation and complying with government regulations for mandatory reporting to government agencies can be complicated. Together, these administrative tasks are taking away valuable clinician time that can otherwise be spent on improving the standard of care for their patients.

SUMMARY OF THE DESCRIPTION

In one embodiment, a web portal is provided by a medical equipment provider for use by customers of the provider and for use by patients of the customers, and the customers can be a plurality of medical centers (e.g., hospitals, clinics, etc.). The web portal can provide, for each medical center, an integration of patient information and equipment information at a single point of access such that the equipment being used (or otherwise in inventory) and the patients using the equipment can be tracked and managed at the single point of access.

In one embodiment, a new equipment record is created and stored in an equipment module when the medical equipment provider provides the new equipment to a customer. When the customer logs into the web portal, the new equipment, as a result of the creating and storing into the equipment module, is shown in the customer's inventory, and the customer can then assign the new equipment to a particular patient of the customer by using the web portal's user interface to perform this assignment. The assignment can be before or after providing (e.g. implanting) the new equipment into the particular patient. This user interface allows the customer to create a patient record for this particular patient and the resulting information is stored in a data structure controlled by the medical equipment provider and is accessible to the customer and, in one embodiment, also to the medical equipment provider through the web portal. The user interface, in one embodiment, can display a summary page (or set of pages) for a medical center (or other customers) that will show all patients of the medical center having been provided with medical equipment from the medical equipment provider and show all inventory of the medical equipment that is in the possession of the medical center. The user interface can allow, in one embodiment, a customer to sort information by patient or equipment type, or dates (such as date of implanting of equipment) or product identification information (e.g., serial numbers), etc. The user information can also show, for each patient of the customer, maintenance reminders or To-Do's or reminders for equipment anniversaries. In one embodiment, the To-Do's or the maintenance reminders or reminders for equipment anniversaries can be established by or based on rules created or managed by the medical equipment provider. In one embodiment, the user interface can receive, from the customer or the patient, reports of product incidents (such as potential problems or issues with the medical equipment). The user interface can also provide links to information resources (such as patient education materials, reference materials, customer training materials, links to other web sites, etc.).

In one embodiment of the user interface, a mapping module, provided through the web portal, can provide a map to a patient showing on one or more maps all of the medical centers in an area that can provide support or treatment for the patient's medical equipment provided by the medical equipment provider. The maps can be used to plan a trip by the patient or when the patient moves or relocates to another geographic area.

In one embodiment, the information maintained in the one or more databases used with the web portal can be used for regulatory compliance reporting, such as reporting to the U.S. FDA (U.S. Food and Drug Administration).

Other features of the present invention will be apparent from the accompanying drawings and from the detailed description which follows.

The above summary does not include an exhaustive list of all aspects of the present invention. It is contemplated that the invention includes all systems and methods that can be practiced from all suitable combinations of the various aspects summarized above, and also those disclosed in the Detailed Description below.

BRIEF DESCRIPTION OF THE DRAWINGS

The invention may best be understood by referring to the following description and accompanying drawings that are used to illustrate embodiments of the invention. In the drawings.

DESCRIPTION OF EMBODIMENTS

Figure 1:
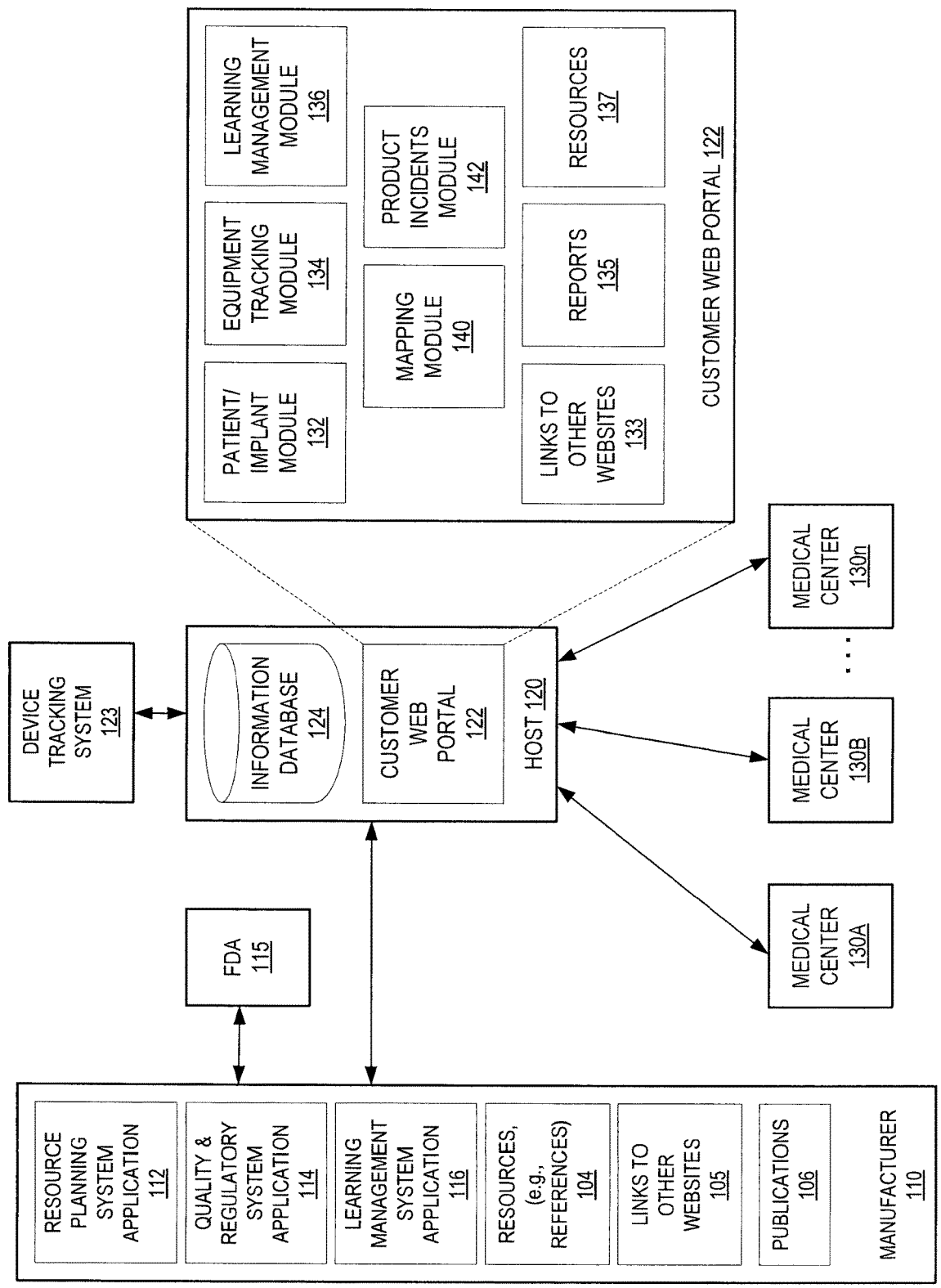
FIG. 1 illustrates an exemplary environment in which a customer web portal can be used, according to one embodiment of the invention; this environment can include one or more private or public networks and can include the Internet.

In the following description, numerous specific details are set forth. However, it is understood that embodiments of the invention may be practiced without these specific details. In other instances, well-known circuits, structures and techniques have not been shown in detail in order not to obscure the understanding of this description.

As used herein, a "user" or "users" is an authorized person or persons that have access to the customer web portal according to embodiments of the invention. A user can be a clinician (e.g., a surgeon, a physician, a nurse), a coordinator, a staff member of a medical center, or other community resource, or a patient or a caregiver of a patient or a relative of a patient. Unless stated otherwise, a user can only view and access information and data with respect to the medical center associated with the user. A "patient" or "patients" is a person or persons who is or will be a recipient of one or more pieces of medical equipment. A piece of "medical equipment" is a piece of equipment that assists a patient with bodily functions. A piece of "medical equipment" can be an implantable device or device-related accessory that is implantable within a human body, or can be a non-implantable device or device-related accessory that remains entirely or partially external to the human body. For example, the medical equipment can be an implantable left ventricle assist device such as a Heartmate II from Thoratec Corporation of Pleasanton, Calif. As another example, the medical equipment can be an insulin pump that is attachable on or implantable into a patient or carried/worn by the patient.

To reduce the administrative overhead incurred by medical centers in managing medical equipment inventory and medical equipment and patient records, embodiments of the present invention disclose a manufacturer-provided customer web portal that offers a single point of access to information and data related to the medical equipment sold or otherwise provided by the manufacturer. It will be understood that such a manufacturer is a medical equipment provider, and another example of a medical equipment provider is an entity that designs the medical equipment but has the medical equipment manufactured by another entity. This web portal can be implemented via cloud computing indirectly managed (e.g., controlled) by the manufacturer or directly managed on-site by the manufacturer. The customer web portal can leverage the information and data that may already be maintained by the manufacturer's internal systems, and provides a centralized information database to store medical equipment and patient data to reduce the redundancy for storing such data at the medical centers. Furthermore, the customer web portal provides a single point of access to assist medical centers with maintaining compliance with applicable protocols, guidelines and regulatory requirements, and to assist medical centers with the ongoing care of patients by providing access to up-to-date news and resources.

FIG. 1 illustrates a block diagram of an environment 100 in which a customer web portal 122 according to embodiments of the invention may be used. A medical equipment manufacturer 110 may have its own internal systems for managing the interactions between the medical equipment manufacturer 110 and medical centers 130A-n and between the medical equipment manufacturer 110 and government agencies such as the Food and Drug Administration (FDA) 115. For example, in one embodiment, the medical equipment manufacturer 110 may use an internal resource planning system (RPS) application 112 to manage the sales and shipments of medical equipment that the medical equipment manufacturer 110 sells. The RPS 112 may keep track of what products have been sold or rented to which account or which medical center 130A-n. The medical equipment manufacturer 110 may use an internal quality and regulatory system (QRS) application 114 to keep track of product incidents and to comply with government regulations (e.g., FDA reporting requirements). In addition, the medical equipment manufacturer 110 may use an internal learning management system (LMS) application 116 to provide training and certification services to clinicians at medical centers 130A-n. In one embodiment, the manufacturer 110 can also use a device tracking system 123 that can be maintained as part of host 120 or as part of manufacturer's internal systems, and this device tracking system 123 can be configured to interact with only employees or other agents of manufacturer 110. Device tracking system 123 can include an application and database that together provide a user interface used by such employees or agents to interact with the web portal 122; for example, the device tracking system 123 can be used to track all shipped devices through the life cycle of each device (medical equipment). In one embodiment, the device tracking system 123 can also be used to generate reports for regulatory requirements, such as reports for FDA requirements. Manufacturer 110 can also include storage for (or links to) information resources such as links to other web sites 105, copies of patient education and references 104 and publications 106. These information resources may be accessible through the web portal 122 such that a web page obtained through web portal 122 can retrieve and display these information resources.

These internal system applications (RPS 112, QRS 114, the device tracking system 123, and LMS 116) used by the medical equipment manufacturer 110 are communicatively coupled to a host 120. The host 120 may be an external host maintained by a third-party, or the host 120 may be an internal host maintained by the medical equipment manufacturer 110. The host 120 hosts the customer web portal 122, for example, on the cloud, and may also include an information database 124 or some other data storage structure to store information and data such as patient records and equipment records related to the medical equipment sold by the medical equipment manufacturer 110. It will be appreciated that host 120 can be one or more computer systems such as a combination of database servers and web servers. The host 120 can be communicatively coupled to the medical centers 130A-n through one or more networks such as the Internet such that each medical center can access the customer web portal 122 through the World Wide Web. The customer web portal 122 provides an integration platform to allow some of the information and data maintained by the medical equipment manufacturer's internal system applications (RPS 112, QRS 114, and LMS 116) to be reflected in the customer web portal 122 to provide a single point of access for each medical center to administer equipment and patient information tracking. Each medical center 130A-n, upon purchasing the web portal in one embodiment, will have an account with the customer web portal 122 such that only authorized users associated with the account would be able to log on to the customer web portal 122 to access the information and data related to the particular medical center. In one embodiment, the authorized user at a medical center can be authenticated through the use of passwords or other authentication techniques known in the art.

When medical equipment such as a medical device or device-related equipment is shipped to a medical center, the medical equipment manufacturer 110 enters the shipping information in its internal RPS 112 to create an equipment record, or further populate the existing equipment record belonging to the medical center where the equipment is shipped. Through the integration of information and data sharing between the RPS 112 and customer web portal 122, the equipment record entered in RPS 112 becomes readily available in the customer web portal 122 to inform the medical center, in one embodiment, of the incoming shipment and to allow the medical center to track the shipment. Upon physical receipt of the medical device or device-related equipment, the receiving medical center can access the customer web portal 122 to view their inventory, add patient data and link a patient to the medical equipment when the equipment is assigned to or used by a patient. A coordinator at the medical center can also update equipment records or enter product incidents or issues related to the medical equipment. Through the integration of information and data sharing between QRS 114 and customer web portal 122, the product incident records are reflected in the medical equipment manufacturer's internal QRS 114 for issues and resolution tracking. In addition, the system can display in one embodiment completed coursework by a medical center, and the medical center's training and certification status (on using the manufacturer's equipment) can be tracked within the customer web portal 122 through the integration of information and data sharing between LMS 116 and customer web portal 122. Furthermore, to support patients after the patients are discharged from a medical center, locations of medical facilities and community resources that have the ability to provide support and service the medical equipment nearby a target location, between an origin and a destination, or at a location where ever the patient travel to, can be obtained through the customer web portal 122. Some of the information and data shared between the medical equipment manufacturer's internal system applications (RPS 112, QRS 114, and LMS 116) and the customer web portal 122 can be stored in an information database 124 of host 120 to avoid redundancies of having to store the same information and data in multiple storage locations.

Referring back to FIG. 1, according to one embodiment of the invention, the customer web portal 122 includes a patient information tracking module 132 which can be considered an implant tracking module when the equipment is an implantable device, an equipment tracking module 134, a learning management module 136, a mapping module 140, and a product incidents module 142. The details of each of these modules in the customer web portal 122 may be described with specific references to implantable medical devices such as heart pumps and related accessories. However, it should be understood that the functionalities and operations of the customer web portal 122 and its modules can be applied to any medical equipment, including non-implantable medical devices and device-related accessories. Furthermore, while the functionalities and operations of the customer web portal 122 will be described with respect to specific modules of the customer web portal 122, it should be understood that particular functions and/or operations of a specific module can be performed by a different module, one or more modules and their functionalities and operations can be integrated into the same module, and different modules can be linked together and operate in synchrony with each other. In one embodiment, the web portal can provide a set of web pages, accessed by an authenticated medical center that provides patient/implant tracking through patient module 132 and provides equipment tracking through equipment tracking module 134 and provides other functions through the other modules shown in the web portal 122 shown in FIG. 1. The web portal 122 can also include one or more web pages with information resources such as links to other websites 133, copies of publications or reports 135 and other resources 137, such as those provided by manufacturer 110 (e.g., resources 104 and/or publications 106 and/or links to web sites 105).

Equipment Tracking Module

The equipment tracking module 134 maintains, for each medical center, equipment records of all medical equipment that has been shipped from the medical equipment manufacturer 110 to the particular medical center, and allows users at the particular medical center to view an equipment list that lists all medical equipment (e.g., all medical equipment provided by manufacturer 110 to the particular medical center) for which an equipment record is maintained. The equipment list can be sortable by equipment name, patient, equipment type, shipment date, location, serial number, or lot number in one embodiment. The equipment tracking module 134 also maintains an inventory list for each medical center. The inventory list differs from the equipment list in that the equipment list includes both medical equipment that are currently used by patients of a medical center (e.g., implanted in patients and non-implantables supporting the implanted equipment) as well as medical equipment that are available for new patients of that medical center, whereas the inventory list only includes medical equipment that are available for new patients of the medical center. Medical equipment that is available for new patients includes medical equipment that is physically at the medical center or medical equipment that is in transit to the medical center. The equipment tracking module 134 allows users to view a particular medical equipment's detailed history including which patients have used the particular medical equipment and any product incidents or complaints. In addition, the equipment tracking module 134 can facilitate set up of equipment maintenance reminders and reminders for equipment usage anniversaries in a displayable Equipment-To-Do list to assist medical centers with on-going patient care and equipment maintenance.

Figure 2:
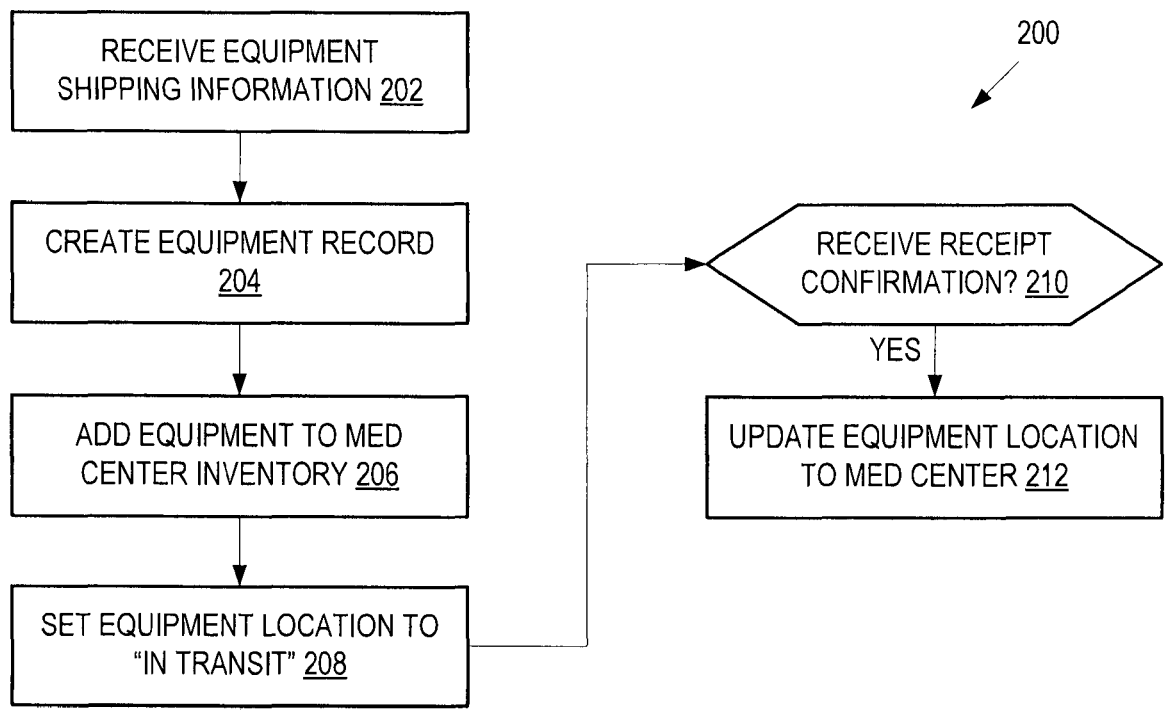
FIG. 2 illustrates a flow diagram for creating an equipment record, according to one embodiment of the invention.

FIG. 2 illustrates a method 200 performed by the equipment tracking module 134 to create an equipment record according to one embodiment. When the medical equipment manufacturer 110 ships out medical equipment and enters the shipping information in the manufacturer's internal RPS 112 or other internal sales or shipping management system, the shipping information can be configured to be automatically sent to the host 120 electronically. The shipping information may include an account ID corresponding to the receiving medical center, and an equipment type corresponding to the type of medical equipment that is being shipped. The equipment type can be, for example, a heart pump, a system controller for the heart pump, a battery module for the heart pump, an apical coring knife, an apical sewing ring, a sealed inflow conduit, a sealed outflow graft, a set of thread protectors, a coring punch, or other heart pump related accessories and ancillary equipment. The medical equipment shipping information may also include a serial number and/or a lot number of the medical equipment.

At block 202, the shipping information entered by the medical equipment manufacturer is received and processed by the equipment tracking module 134. At block 204, in response to receiving the medical equipment shipping information, an equipment record is created, for example, electronically on the host, for each piece of medical equipment being shipped. In one embodiment, the equipment record may include fields for some or all of the shipping information including an account ID field, an equipment type field, a serial number field and/or a lot number field. In addition, the equipment record also includes a location field to indicate the current location of the medical equipment, and a patient field that is used to associate the equipment record with a patient record. It should be noted that, in one embodiment, only the medical equipment manufacturer can create an equipment record, and the creation of the equipment record for the customer web portal 122 is initiated at the time of shipment. However, details associated with this equipment record may be modified or changed by a user at the medical center. In one embodiment, the equipment record may be stored in the information database 124 of host 120.

At block 206, the medical equipment is added to the receiving medical center's inventory list, and at block 208, the location field of the equipment record is set to "in transit" or "in transfer." At this point, when a user associated with the receiving medical center (i.e. the medical center corresponding to the account ID) accesses the customer web portal 122, the medical equipment that is being shipped is listed in the receiving medical center's inventory list with a location of "in transit" or "in transfer" to notify the user that the medical equipment has been shipped.

At block 210, in one embodiment which uses receipt confirmation, it is determined if a receipt confirmation is received from the medical center. The receipt confirmation may be generated when a user at the receiving medical center accesses the customer web portal 122 and modifies the location field of the equipment record upon receiving the medical equipment at block 212. If no receipt confirmation is received, the shipment is presumed to still be in transit. If a receipt confirmation is received, the location field of the equipment record is updated to the location of the receiving medical center. In an embodiment that uses receipt confirmation, once the location field of the equipment record is updated to the location of the receiving medical center, the equipment record becomes available for association with a patient record of any patient at the medical center.

Implant/Patient Information Tracking Module

The patient information tracking module 132 maintains, for each medical center, patient records of patients that are either assigned to or are waiting to be assigned to one or more pieces of medical equipment. The patient information tracking module 134 allows users at a medical center to assign one or more pieces of medical equipment to a patient by associating the equipment record(s) of the medical equipment(s) with a patient record. A patient record can be associated with one or more equipment record if more than one piece of medical equipment is assigned to a patient (e.g., a heart pump and a battery). However, an equipment record can only be associated with one patient record in one embodiment. The patient information tracking module 134 can also allow a patient record and equipment record(s) that is associated with that patient record to be transferred to another account (i.e. another medical center) if the patient is being transferred to another medical center or the patient and patient record can be associated with multiple medical centers in one embodiment.

A patient can be categorized as a candidate for a procedure/implant, a post-operation patient, or a discharged patient in one embodiment. The patient information tracking module 132 can allow a user to view a list of candidates, a list of post-operation patients, and a list of discharged patients for a particular medical center. Each category can be customizable, and each listing can be sorted by first name and last name. In one embodiment, customization can be performed through an administration web page within the web portal 122. A patient is categorized as a candidate if a patient record has been created for that patient and there is no implant record associated with the patient record, indicating that the patient has not yet been equipped, associated, or implanted with the medical equipment. A patient is categorized as a post-operation patient if one or more implant records with no discharge date are associated with the patient record of the patient and there is no outcome date associated with the patient, indicating that the patient has been implanted with the medical equipment, but has not yet been discharged from the medical center. A patient is categorized as a discharged patient if one or more implant records are associated with the patient record of the patient and there is a discharge date associated with the implant but no outcome date associated with the patient, indicating that the patient has been discharged from the hospital and is currently using the medical equipment. A patient that has an outcome date associated with patient indicates that the patient is no longer using or associated with the medical equipment (e.g., patient received a transplant to replace the implanted medical equipment, recovered and does not require the aid of the medical equipment, or expired, etc.). A patient that has an outcome date associated with the patient is not listed in the list of candidates, the list of post-operation patients, or the list of discharged patients.

Figure 3:
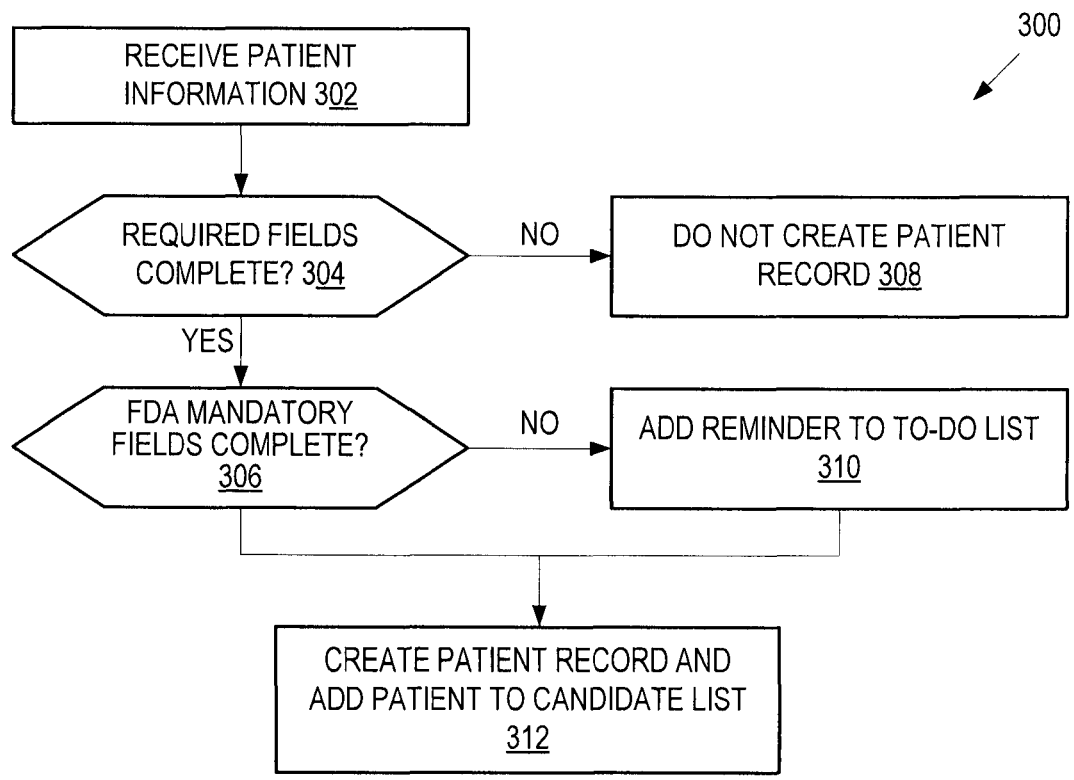
FIG. 3 illustrates a flow diagram for creating a patient record, according to one embodiment of the invention.

FIG. 3 illustrates a method 300 performed by the patient information tracking module 132 to (electronically) create a patient record according to one embodiment. When a patient is admitted to a medical center, a user at the medical center enters patient information in the customer web portal 122. At block 302, the patient information is received by the patient information tracking module 132. At block 304, it is determined if the patient information includes all required fields for creating a patient record. In one embodiment, the required fields for creating a patient record include the name of the patient and either a social security number of the patient or a medical record number of the patient. If it is determined that the patient information does not have all the required fields for creating a patient record, then at block 308, the patient record is not created.

If it is determined that the patient information does have all the required fields for creating a patient record, then at block 306, it determines if the patient information includes all mandatory fields required by government regulations used for regulatory reporting. In one embodiment, the mandatory fields are FDA mandatory fields that may include the patients' address and telephone number. In one embodiment, the patient information is encrypted using techniques known in the art. If it is determined that the patient information does not have all the mandatory fields required by government regulations, then at block 310, a regulatory compliance reminder is added to a displayable Patient-Care-To-Do list for the medical center. Regardless of whether all mandatory fields required by government regulations are provided, a patient record is created, and the patient's name is added to the list of candidates. In one embodiment, the patient record may be stored in the information database 124 of host 120.

According to one embodiment, the patient record can include a patient name field, a patient address field, patient social security number, hospital record ID number, and a patient phone number field to identify the patient. The patient record can also include an operation or implant date field, a medical center field, a surgeon field, a follow-up physician field, an implant duration or post-operation duration field, and a discharge date field. The patient record can also include a list of current and past medical equipment that are currently assigned or have been assigned to the patient. In another embodiment, the patient record may further include personal data fields such as age, weight, height, and gender fields. The patient record may also include an etiology field to indicate the medical condition that the patient is suffering from and an outcome field and an outcome date field to indicate the post-operation outcome of the patient.

Figure 4:
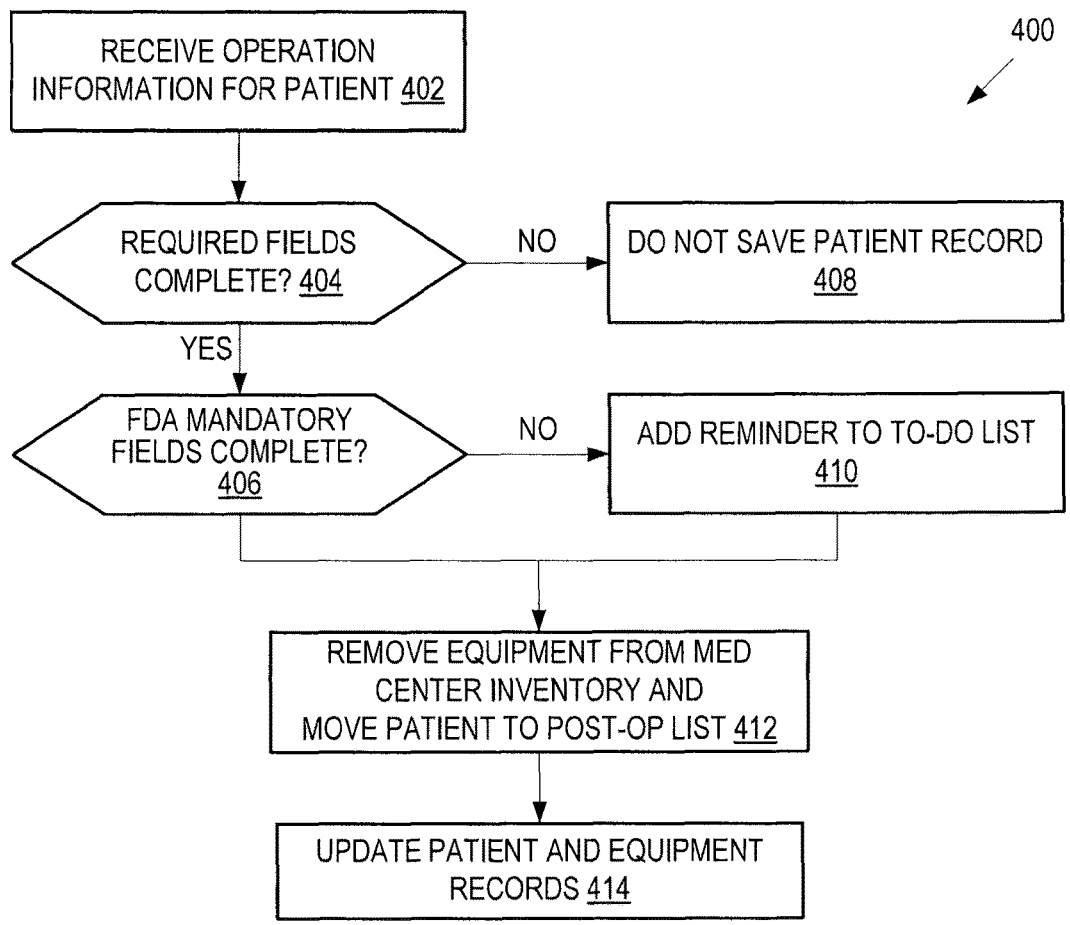
FIG. 4 illustrates a flow diagram for assigning medical equipment to a patient, according to one embodiment of the invention.

FIG. 4 illustrates a method 400 performed by the patient information tracking module 132 for assigning medical equipment to a patient according to one embodiment. When medical equipment is available for a candidate patient, a coordinator or user at the medical center schedules a medical operation to be performed on the patient to equip, implant, or generally improve the condition of the patient with the medical equipment. The coordinator or user enters the operation information into the patient record in the customer web portal 122. At block 402, the operation information is received by the patient information tracking module 132. At block 404, it is determined if the operation information includes all required fields to associate the patient record of the patient with the equipment record corresponding to the medical equipment being assigned. In one embodiment, the required fields for associating a patient record with an equipment record include an operation or an implant date and a serial number or a lot number corresponding to the medical equipment being assigned. If it is determined that the operation information does not have all the required fields to create the implant record, then at block 408, the patient record is not updated with the medical equipment assignment information.

If it is determined that the operation information does have all the required fields to associate a patient record with an equipment record, then at block 406, it is determined if the operation information includes all mandatory fields required by government regulations that are used for regulatory reporting. In one embodiment, the mandatory fields are FDA mandatory fields that may include the name, address, and telephone number of the surgeon performing the implantation or operation to equip the patient with the medical equipment, and the name, address, and telephone number of the follow-up physician for the patient and other information such as device serial number or lot number. If it is determined that the operation information does not have all the mandatory fields required by government regulations, then at block 410, a regulatory compliance reminder is added to a displayable Patient-Care-To-Do list for the medical center. Regardless of whether all mandatory fields required by government regulations are provided, at block 412, the medical equipment that is being assigned is removed from the inventory list of the medical center, and the patient's name is moved from the list of candidates to the list of post-operation patients. At block 414, the patient record and the equipment record are updated to reflect the assignment of the medical equipment to the patient by adding the medical equipment to the list of current medical equipment that are currently assigned to the patient in the patient record, and by adding the patient's name to the patient field of the equipment record.

Figure 5:
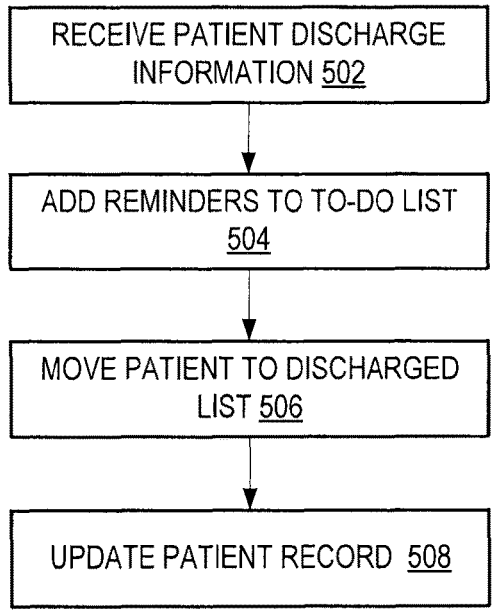
FIG. 5 illustrates a flow diagram for discharging a patient, according to one embodiment of the invention.

FIG. 5 illustrates a method 500 performed by the patient information tracking module 132 for assisting a medical center with discharging a patient from a medical center. Once a patient has been operated on and equipped with the medical equipment, a patient may remain at the medical center for a short period of time for observation. When the patient is discharged from the medical center after the observation period, a user enters patient discharge information in the customer web portal 122. In one embodiment, the discharge information may include a discharge date. At block 502, the patient discharge information is received by the patient information tracking module 132. At block 504, in one embodiment, patient care reminders and equipment usage anniversaries (e.g., implant anniversaries) reminders are automatically added to the Patient-Care-To-Do list. In one embodiment, the patient care reminders may be reminders for clinicians at the medical center to check up on the discharged patient, reminders for the patient to visit the medical center for medical equipment maintenance such as changing the battery every six months, or reminders to provide education on the medical device to the patient or family members of the patient. The anniversaries reminders, for example, can be reminders for the one-year, two year, five-year anniversaries, or any other chosen annual period from the operation or of the implantation to notify the patient of the milestones. At block 506, the patient's name is moved from the list of post-operation patients to the list of discharged patients. At block 508, the implant record is updated by adding the discharge date to the discharge date field, and the patient record is also updated with last discharged date.

Figure 6:
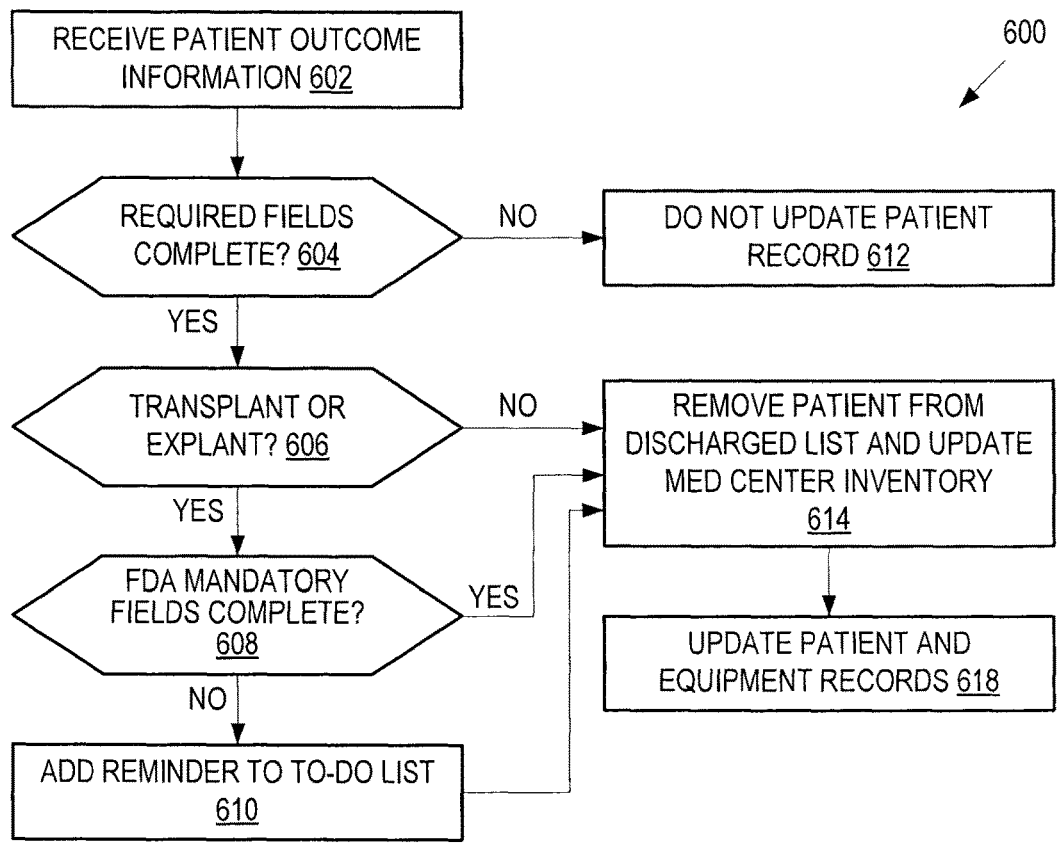
FIG. 6 illustrates a flow diagram for tracking the outcome of a patient, according to one embodiment of the invention.

FIG. 6 illustrates a method 600 performed by the patient information tracking module 132 for tracking the outcome of a patient of a medical center. An outcome is a post-operation event, and can include a transplant, a recovery, an explant, or an expiration of the patient. A transplant indicates that the medical equipment has been replaced with a donated organ and the patient no longer requires the use of the medical equipment. A recovery indicates that the patient has fully recovered from medical condition that the patient was suffering from, and the patient no longer requires the use of the medical equipment. An explant indicates that the patient is no longer using or no longer equipped with the medical equipment. This situation may occur, for example, if the patient switches to medical equipment from a different manufacturer. An expiration of the patient indicates that the patient has deceased and no longer requires the use of the medical equipment.

When a medical center is informed or learns of the outcome of a patient, a user enters the patient outcome information into the customer web portal 122. At block 602, the patient outcome information is received by the patient information tracking module 132. At block 604, it is determined if the patient outcome information includes all required fields for tracking the outcome of the patient. In one embodiment, the required fields for tracking the outcome of the patient include an outcome date and an outcome. If it is determined that the patient outcome information does not have all the required fields to track the outcome of the patient, then at block 612, the patient record is not updated with the outcome information.

If it is determined that the patient outcome information does have all the required fields to track the outcome of the patient, then at block 606, it is determined if the outcome is one of a transplant or an explant. If it is determined that the outcome is a transplant or an explant, then at block 608, it is determined if the patient outcome information includes all mandatory fields required by government regulations that are used for regulatory reporting. In one embodiment, the mandatory fields are FDA mandatory fields that may include the name, address, and telephone number of the transplant or explant surgeon that performed the removal of the medical equipment. If it is determined that the patient outcome information does not have all the mandatory fields required by government regulations, then at block 610, a regulatory compliance reminder is added to a displayable Patient-Care-To-Do list for the medical center. Regardless of whether the outcome is a transplant or an explant, or whether all mandatory fields required by government regulations are provided, at block 614, the medical equipment that has been assigned to the patient may be added back into the inventory list of the medical center in certain embodiments, and the patient's name is removed from list of discharged patients. At block 618, the patient record and the equipment record are updated by moving the medical equipment from the list of current medical equipment assigned to the patient to the list of past medical equipment in the patient record, and by removing the patient's name from the patient field of the equipment record.

Product Incidents Module

The product incidents module 142 maintains product incident records and facilitates the submission and resolution of product incidents. The product incidents module 142 allows users at a medical center to enter product incident information in the customer web portal 122 to create product incident records and to submit product incident reports to the medical equipment manufacturer for investigation. The product incident information includes a short description of the product failure such as a description of a defect or a malfunction of the medical equipment. In one embodiment, a product incident may have a status that is either open, submitted, investigation pending, investigation completed, or investigation summary issued, or duplicate product incident. A product incident is "open" if a product incident record has been created but a product incident report has not yet been submitted to the medical equipment manufacturer. A product incident has a status of "submitted" if the product incident report corresponding to the product incident has been sent to the medical equipment manufacturer. An "investigation pending" status indicates that the medical equipment manufacturer has received the Product Incident report and the investigation is either underway or awaiting product return. An "investigation completed" status indicates that the medical equipment manufacturer has completed its investigation of the product incident. An "investigation summary issued" status indicates that the medical equipment manufacturer has issued an investigation report summarizing the findings of the related product incident and the product incident report is closed.

A product incident record created for a product incident can be associated with an account (i.e., the medical center submitting the product incident information), one or more equipment records corresponding to the medical equipment that is failing, and a contact person who is typically the user who is entering the product incident information. A product incident record can optionally be associated with a patient record if the product incident occurred while the medical equipment is in use by or implanted in a patient. According to one embodiment, the product incident record includes an account field, a patient field, and an equipment field to identify which medical equipment is failing, and a status field to indicate the status of the product incident. The product incident record may also include a contact information field, a priority field, and a product incident status field. The product incident record can further include an event date field, a communication date field, a short description field, a supplemental information field, and an investigation summary field and other fields.

Figure 7:
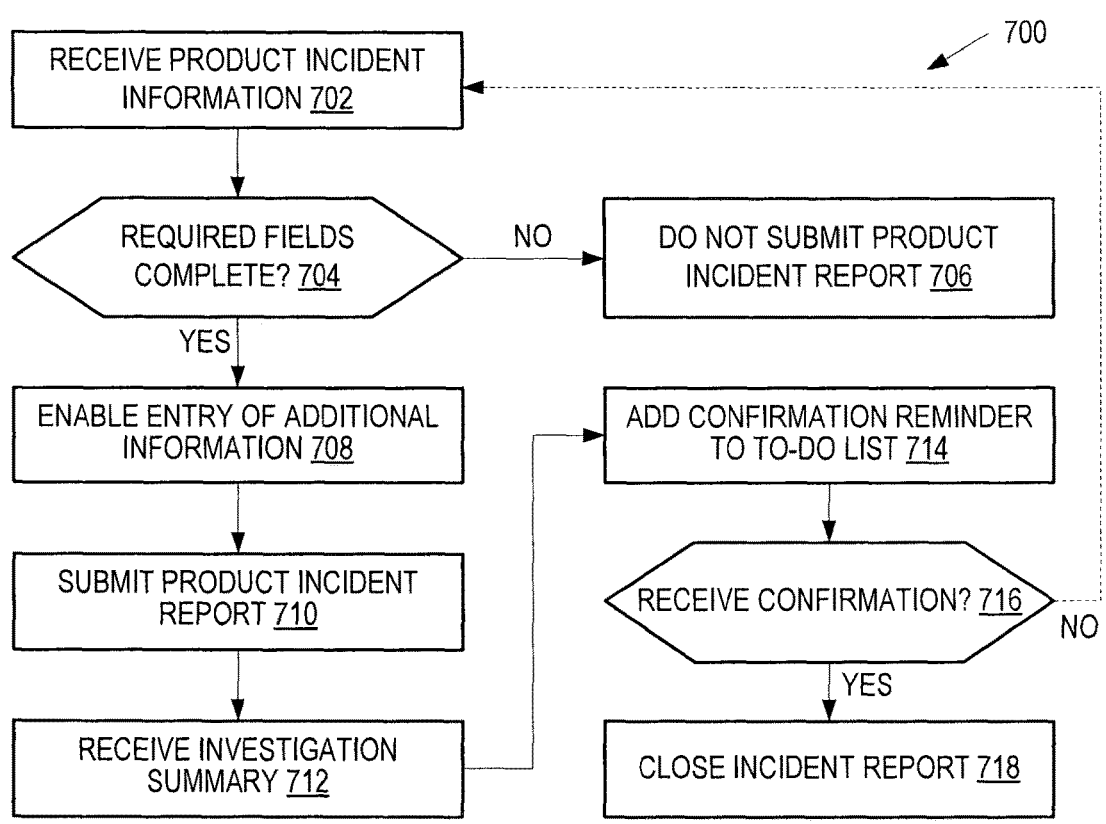
FIG. 7 illustrates a flow diagram for tracking product incidents related to medical equipment failures, according to one embodiment of the invention.

FIG. 7 illustrates a method 700 performed by the product incidents module 142 for tracking product incidents associated with the medical equipment sold by the medical equipment manufacturer 110. When a product incident occurs such as an equipment failure or an equipment malfunction, a user accesses the equipment record associated with the medical equipment and enters product incident information into the customer web portal 122. At block 702, the product incident information is received by the product incidents module 142. When the product incident information is received, a product incident record is created. In one embodiment, the product incident record may be stored in the information database 124 of host 120. The account field, equipment field, and contact field of the product incident record can be automatically populated in one embodiment with the corresponding information based on the login information of the user and the equipment record that the user accessed to enter the product incident information. The product incident status field is also automatically populated with the status as "open."

At block 704, it is determined if the product incident information includes all required fields for submitting a product incident report to the medical equipment manufacturer 110. In one embodiment, the required fields for submitting a product incident report to the medical equipment manufacturer include an event date and a short description of the product incident and other fields that are known in the art for product incident reports. If it is determined that the product incident information does not have all the required fields for submitting a product incident report to the medical equipment manufacturer, then at block 706, the product incident report is not submitted to the medical equipment manufacturer. It is advantageous to include the operations of block 704 to check for required fields because once a product incident report is submitted to the medical equipment manufacturer, under some government regulations, the submission may trigger a strict deadline for the medical equipment manufacturer to resolve the product incident regardless of whether adequate information has been submitted or not. By determining if all require fields have been provided before submitting the product incident report, the medical equipment manufacturer can make sure that there is adequate information for the medical equipment manufacture to resolve the product incident before the time period for resolution starts.

If it is determined that the required fields for submitting a product incident report to the medical equipment manufacturer have been provided and the report is submitted, then at block 708, in one embodiment, the entry of additional information that may aid with the investigation is enabled. The user may enter additional information such as images of the equipment defect or equipment malfunction; this additional information may be added as an attachment. The entry of additional information is disabled prior to determining if the product incident information includes all required fields for the reason of ensuring that required fields such as an event date and a short description of the product incident are always submitted with any additional information. At block 710, a product incident report is submitted to the QRS 114 of the medical equipment manufacturer 110, and the product incident status field of the product incident record is updated to "submitted." In another embodiment, the entry of additional information is disabled until the product incident report is submitted.

Once the medical equipment manufacturer 110 receives the product incident report in its internal QRS 144, the medical equipment manufacturer 110 investigates the product incident. This may require the medical center to ship the medical equipment to the medical equipment manufacturer 110. Once the investigation is completed by the medical equipment manufacturer 110, the medical equipment manufacturer 110 enters an investigation summary describing the findings in its internal QRS 144. The investigation summary is then sent to the host 120. The investigation summary field in the product incident record is updated with the investigation summary, and the product incident status field of the product incident record is updated to "investigation summary issued." Then at block 714, a confirmation reminder is added to the Equipment-To-Do list to remind a user at the medical center that submitted the product incident report to confirm the findings of the medical equipment manufacturer 110. At block 716, it is determined if a confirmation is received. If a confirmation is received, then at block 718, the product incident status field of the product incident record is updated to "closed." If the user is dissatisfied with investigation summary, the user can optionally submit new product incident information back at block 702.

Learning Management Module

The learning management module 136 will allow users (including doctors, nurses and others at medical centers and also patients) to self-serve their medical equipment training needs by providing users access to all current and future medical equipment training materials through the customer web portal 122. The learning management module 136 links and interfaces to the medical equipment manufacturer's 110 internal LMS 116. In one embodiment, the materials can be specific to the devices and equipment provided by the medical equipment provider and these materials can be provided through the web portal in order to comply with FDA or other regulatory requirements. The learning management module 136 tracks the medical equipment training progress and participation of users, and can be configured to allow for creation and maintaining compliance documentation.

In one embodiment, the learning management module 136 maintains, for each medical center, training information that may include a list of individuals (e.g., clinicians, physicians, surgeons) and the medical equipment that the individuals are trained or certified to handle. The training information may also include a list of the training courses that each individual has completed and the last completion date for each of the training courses. In one embodiment, the training information can be stored in the information database 124 of host 120. In addition, according to one embodiment, the learning management module 136 may automatically add training reminders to the Patient-Care-To-Do list to alert users of upcoming anniversaries of course completion dates to remind individuals at the medical center to take or retake training courses that are required to maintain their certification.

Mapping Module

The mapping module 140 provides users with locations of medical facilities such as medical centers and/or community centers that have the medical staff, training, and/or capability to provide medical equipment support for equipment provided by the medical equipment manufacturer 110 that are nearby one or more target locations. A patient of a medical center may not always live close by to the medical center that equipped or implanted the patient with the medical equipment. When a patient is discharged from the medical center, the patient often requests information of medical facilities that are closer to the patient's home such that the patient can have quicker access from the patient's home to a medical staff that can service or provide support for the medical equipment. Furthermore, with technological advances in medical equipment such as implantable medical devices, patients are becoming more mobile and often travel on long trips with the implanted medical device. When a patient plans a trip, the patient often requests information of medical facilities that are along the route of the trip or near the travel destination such that the patient would have knowledge of the locations of nearby medical facilities that can assist the patient with the medical equipment, if necessary, while the patient is away from home. In order to provide a patient with the locations of such medical facilities that are nearby a target location, a clinician at a medical center has been required to contact the medical equipment manufacturer directly to obtain such information or use the web to identify other centers and call them to confirm qualifications and contact information. Such information has not been readily available because the medical equipment manufacturer has to first access its internal LMS 116 to determine if a particular facility is trained and certified to provide the service and support for the particular piece of medical equipment that the patient is equipped or implanted with. The mapping module 140 allows a user to obtain such information through the customer web portal 122 without having to contact the medical equipment manufacturer directly.

When a patient requests information on medical facilities that are nearby the patient's home or nearby a particular target location, a user enters locality information such as an address or a zip code of the target location into the customer web portal 122. Alternatively, if a patient is planning a trip, the locality information may include source location information (i.e. address or zip code of source location), and one or more destination location information (i.e. addresses or zip codes of destinations). In one embodiment, a user may also enter medical equipment information such as a medical equipment type. When the mapping module 140 receives the locality information, the mapping module 140 communicates with the learning management module 136 to obtain information of medical facilities that are trained or certified to handle medical equipment that are nearby the target location or along a route from the source location to the destination locations. In an alternative embodiment, the mapping module 140 can access the information database 124 of the host 120 to obtain the information of the medical facilities. The results (i.e. the information of medical facilities that are nearby the target location or along the route of a trip) can be displayed on a map. The results may include, for each medical facility, the location of the facility, the hours of operations of medical facility, and the medical equipment types that the facility is able to support. In one embodiment, the results displayed on the map can be filtered by a radius length around the target location or the route of a trip, by a resource type such as whether the medical facility is an implant center or a community resource, or by the medical equipment type that the medical facility is able to support.

To-Do Lists

As mentioned above, according to some embodiments, certain modules such as the patient information tracking module 132, the equipment tracking module 134, and/or the learning management module 136 may automatically add reminders to displayable To-Do lists. In one embodiment, the customer web portal 122 can maintain To-Do lists for each medical center, such as a Patient-Care-To-Do list and an Equipment-To-Do list. The Patient-Care-To-Do list lists reminders that can be related to patient care and may include tasks that are to be performed by users or other individuals at the medical center, or by patients. The Equipment-To-Do list lists reminders that can be related to the medical equipment such as maintenance or replacement intervals for the medical equipment.

In one embodiment, the Patient-Care-To-Do and the Equipment-To-Do lists are displayed in a pop-up window when a user first log on to the customer web portal 122. The Patient-Care-To-Do and the Equipment-To-Do lists are also displayed on a graphical user interface of the customer web portal 122. When a task that is being reminded by a reminder is completed, a user can select the reminder and mark it as completed to remove the reminder from the To-Do list. If a reminder is overdue, the reminder is highlighted or is displayed in a color that is different from other reminders that have future due dates. In one embodiment, when a reminder is overdue, an email notification is sent to the owner or person responsible for performing the task that is the subject of the reminder. In one embodiment, when a reminder is due within a predetermined period of time, an email notification is sent to the owner or person responsible for performing the task that is the subject of the reminder. In yet another embodiment, email notifications are not sent at all in order to encourage users to use the customer web portal 122 as the single point of access for information and data related to the medical equipment sold by the medical equipment manufacturer 110.

Graphical User Interface

Figure 8A:
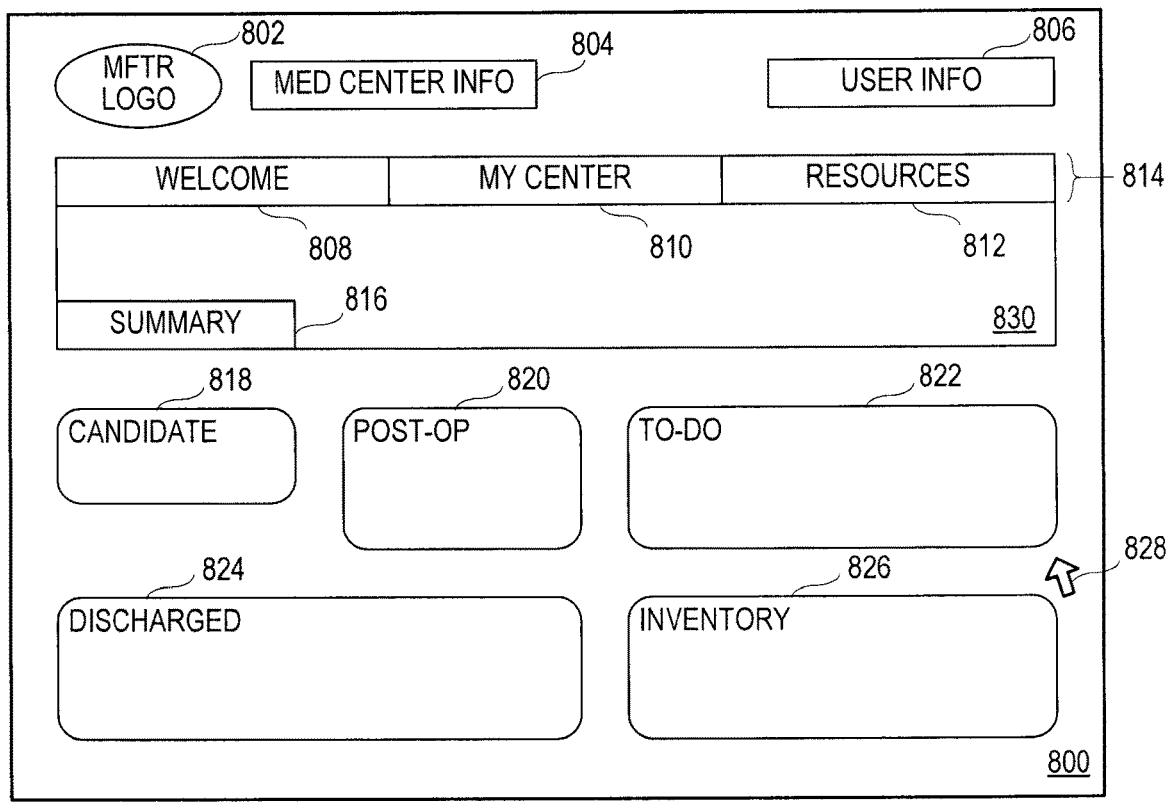
FIG. 8A illustrates one exemplary view of a summary page of the graphical user interface of a customer web portal, according to one embodiment of the invention.

In another aspect of the invention, the customer web portal 122 presents a graphical user interface (GUI) on a display device to a user to enable the user to easily navigate the customer web portal 122 to access the information and data that are maintained or updated by the modules of the customer web portal 122 described above. FIG. 8A illustrates a view of a summary page of the GUI 800 of the customer web portal 122 according to one embodiment. The GUI 800 includes a medical equipment manufacturer logo 802, a medical center information element 804, and a user information element 806. The user information element 806 displays user information about the user that is logged onto the to the customer web portal 122. The user information may include a name of the user and a title or position of the user. The medical center information element 804 displays the name of the medical center associated with the user and may also include address and contact information of the medical center.

The GUI 800 may also include patients list elements such as a candidate list element 818 to display a list of candidates of the medical center that are waiting for medical equipment, a post-operation list element 820 to display a list of post-operation patients of the medical center, and a discharged list element 824 to display a list of discharged patients. A user can select in one embodiment a patient name on any of the patients lists to access information in the patient record of that patient. The GUI 800 may further include a To-Do list element 822 to display the Patient-Care-To-Do and the Equipment-To-Do lists, and an inventory element 826 to display the inventory list of the medical center.

In one embodiment, the GUI 800 includes a navigation pane element 830. The navigation pane element 830 includes a navigation bar element 814 and a page identifier element 816. The navigation bar element 814 may include a welcome link element 808 to take the user to a welcome page, a "My Center" link element 810 to take the user to the summary page, and a resources link element 812 to take the user to a resource page that includes links to the medical equipment manufacture's website, links to downloadable brochures and publications, and links to news articles related to the medical equipment. In other embodiments, the navigation bar element 814 may include other link elements to take the user to other pages. The page identifier element 816 identifies the current page that is being displayed on the GUI 800. A background image may be displayed in the navigation pane element 830.

The position of the navigation pane element 830 in the GUI 800, in one embodiment, is static regardless of what page the user is viewing. While the background image and the page identifier element 816, as well as the other content outside the navigation pane element 830 may change as the user navigates from one page to another, the link elements of the navigation bar element 814 remains the same. This allows the user to easily return to the page of one of the links, for example, the summary page, no matter where the user has navigated to in GUI 800 of the customer web portal 122.

Figure 8B:
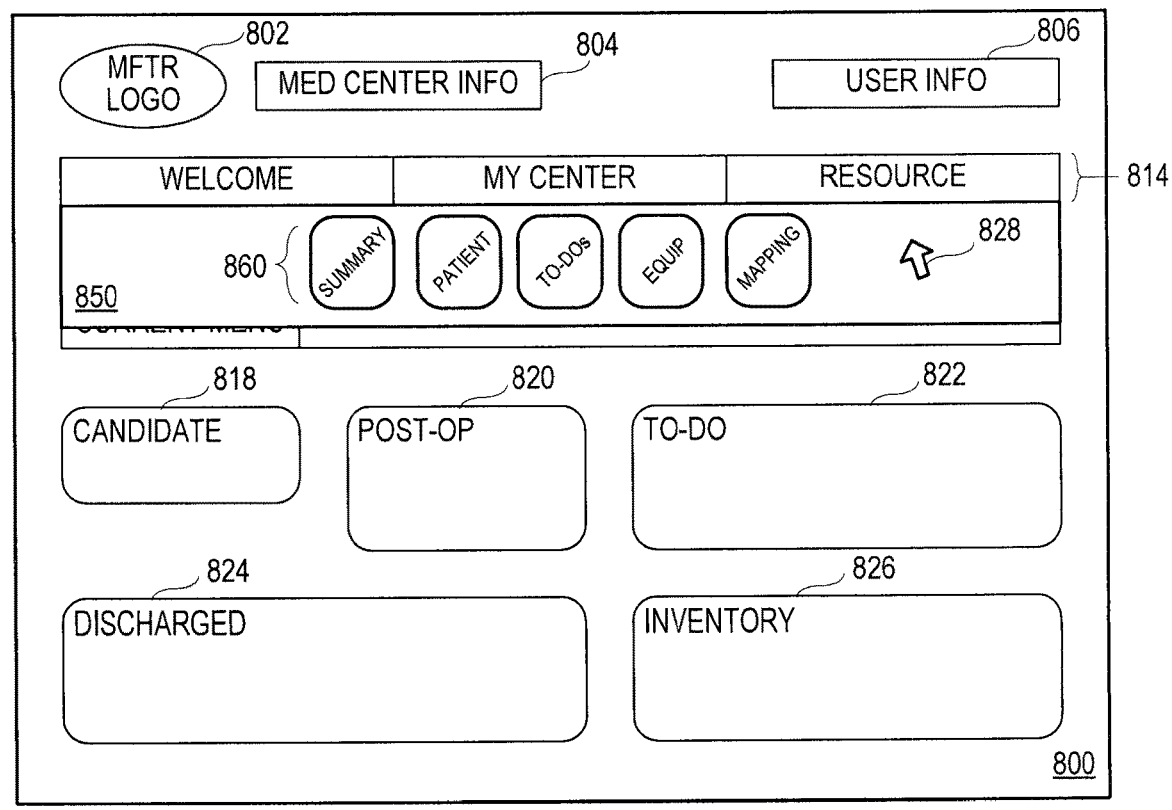
FIG. 8B illustrates another exemplary view of a summary page of the graphical user interface of a customer web portal, according to one embodiment of the invention.

Referring to FIG. 8B, according to one embodiment, when a user positions the cursor 828 over the navigation pane, dynamic element 830 aside from the navigation bar element 814, such as a pop-up navigation interface element 850 is displayed. When a user positions the cursor 828 outside the navigation pane element 830, the pop-up navigation interface element 850 is removed. The pop-up navigation interface element 850 includes one or more page interface elements 860 that are accessible by the user to navigate to corresponding pages. For example, the page interface elements 860 may include a summary page interface element that is accessible by the user to navigate to the summary page to display the contents of the summary page described above. The page interface elements 860 may include a patients page interface element that is accessible by the user to navigate to the patients page to display the patient lists (e.g., list of candidates, list of post-operation patients, and list of discharged patients) and Patient-Care-To-Do list. The page interface elements 860 may include a To-Do interface element that is accessible by the user to navigate to the To-Do page to display the Patient-Care-To-Do and Equipment-To-Do lists. The page interface elements 860 may also include an equipment interface element that is accessible by the user to navigate to the equipment page to display the equipment list of the medical center, the inventory list of the medical center, and the Equipment-To-Do list. Additionally, the page interface elements 860 may include a mapping interface element that is accessible by the user to navigate to the mapping page to allow the user to enter locality information to obtain locations of medical facilities nearby a target location or along a route of a trip.

Figure 9:
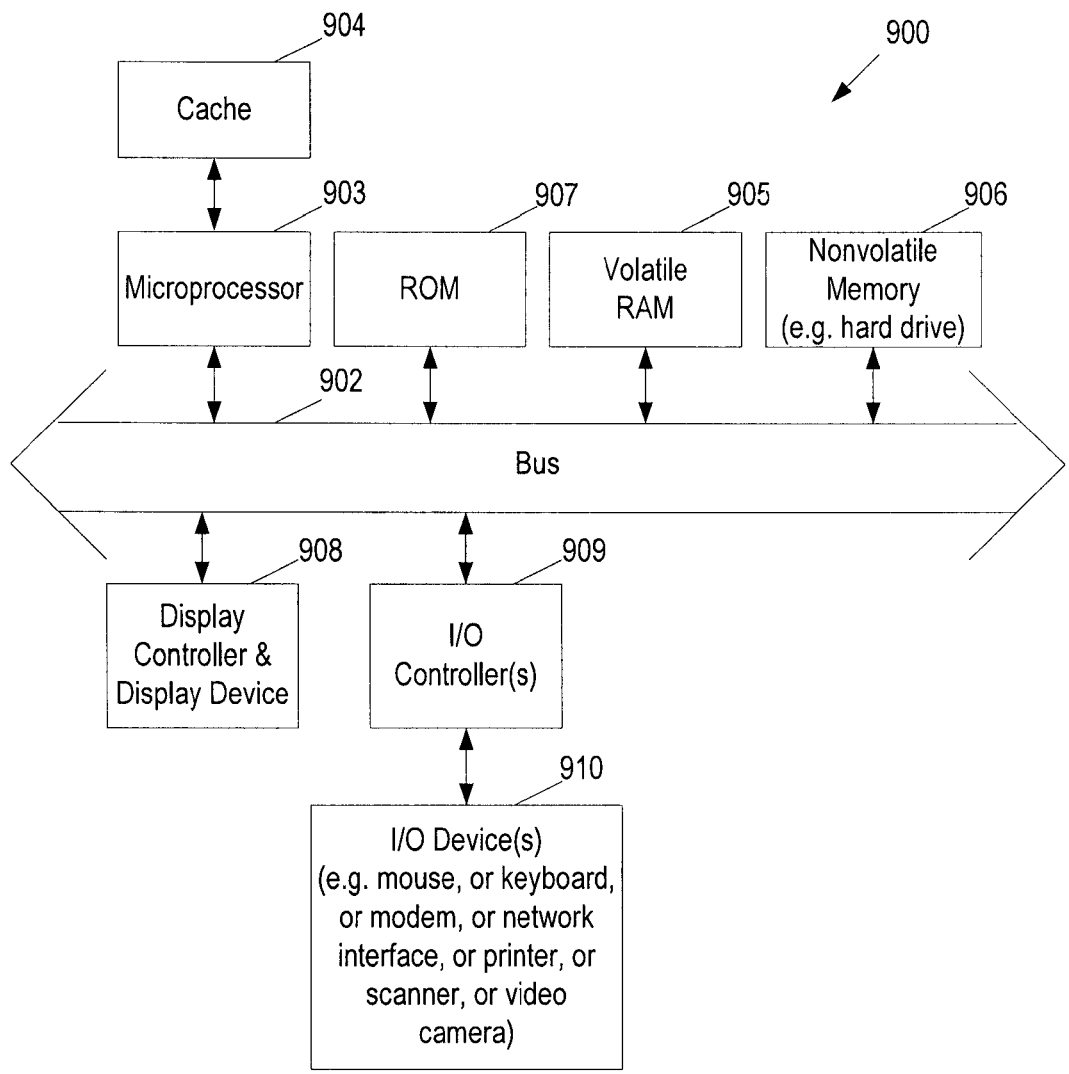
FIG. 9 illustrates a block diagram of an exemplary computing system configured for use with the disclosed embodiments.

FIG. 9 shows one example of a typical computer system or other types of data processing systems which may be used with the disclosed embodiments. For example, it is noted that the processes described with respect to FIGS. 2 through 7 are operational through the example computing system. A medical center may use one or more such systems to access web portal 122 and the web portal 122 (and the associated database systems) can be implemented with one or more data processing systems such as the system shown in FIG. 9. However, it is noted that while FIG. 9 illustrates various components of a computer system, it is not intended to represent any particular architecture or manner of interconnecting the components but rather provides an example representation of how the components and architecture may be configured. It will also be appreciated that network computers and other data processing systems which have fewer components than shown in FIG. 9 or perhaps more components may also be used with the disclosed embodiments. The computer system of FIG. 9 may be any computing system capable of performing the described operations.

As shown in FIG. 9, the computer system 900, which is a form of a data processing system, includes a bus 902 which is coupled to one or more microprocessors 903. In one embodiment, computer system 901 includes one or more of a read only memory (ROM) 907, volatile memory (RAM) 905, and a non-volatile memory (EEPROM, Flash) 906. The microprocessor 903 is coupled to cache memory 904 as shown in the example of FIG. 9. Cache memory 904 may be volatile or non-volatile memory.

The bus 902 interconnects these various components together and in one embodiment interconnects these components 903, 907, 905, and 906 to a display controller and display device 908. The computer system 901 may further include peripheral devices such as input/output (I/O) devices which may be mice, keyboards, modems, network interfaces, printers, scanners, video cameras and other devices which are well known in the art. Typically, the input/output devices 910 are coupled to the system through input/output controllers 909.

The volatile RAM 905 is typically implemented as dynamic RAM (DRAM) which requires power continually in order to refresh or maintain data in the memory. The non-volatile memory 906 is typically a magnetic hard drive, magnetic optical drive, an optical drive, a DVD RAM, a Flash memory, or other type of memory system which maintains data even after power is removed from the system. Typically, the non-volatile memory will also be a random access memory although this is not required.

While FIG. 9 shows that the non-volatile memory is a local device coupled directly to the rest of the components in the data processing system, it will be appreciated that the disclosed embodiments may utilize a non-volatile memory which is remote from the system, such as a network storage device which is coupled to the data processing system through a network interface such as a modem or Ethernet interface.

The bus 902 may include one or more buses connected to each other through various bridges, controllers and/or adapters as is well known in the art. In one embodiment the I/O controller 909 includes a USB (Universal Serial Bus) adapter for controlling USB peripherals, and/or an IEEE-1394 bus adapter for controlling IEEE-1394 peripherals.

It will be apparent from this description that aspects of the disclosed embodiments may be embodied, at least in part, in software (or computer-readable instructions). That is, the techniques, for example the processes of FIGS. 2 through 7 may be carried out in a computer system or other data processing system in response to its processor, such as a microprocessor, executing sequences of instructions contained in a memory, such as ROM 907, volatile RAM 905, non-volatile memory 906, cache 904 or a remote storage device. In various embodiments, hardwired circuitry may be used in combination with software instructions to implement the disclosed embodiments. Thus, the techniques are not limited to any specific combination of hardware circuitry and software nor to any particular source for the instructions executed by the data processing system. In addition, throughout this description, various functions and operations are described as being performed by or caused by software code to simplify description. However, those skilled in the art will recognize what is meant by such expressions is that the functions result from execution of the code by a processor, such as the microprocessor 903.

A machine readable storage medium can be used to store software and data which when executed by a data processing system causes the system to perform various methods of the disclosed embodiments. This executable software and data may be stored in various places including for example ROM 907, volatile RAM 905, non-volatile memory 906 and/or cache 904 as shown in FIG. 9. Portions of this software and/or data may be stored in any one of these storage devices.

Thus, a machine readable storage medium includes any mechanism that stores any information in a form accessible by a machine (e.g., a computer, network device, personal digital assistant, manufacturing tool, any device with a set of one or more processors, etc.) including transitory and non-transitory storage medium. For example, a machine readable medium includes recordable/non-recordable media (e.g., read only memory (ROM); random access memory (RAM); magnetic disk storage media; optical storage media; flash memory devices; etc.).

The detailed description of embodiments of the invention makes reference to the accompanying drawings in which like references indicate similar elements, showing by way of illustration specific embodiments of practicing the invention. Description of these embodiments is in sufficient detail to enable those skilled in the art to practice the invention. One skilled in the art understands that other embodiments may be utilized and that logical, mechanical, electrical, functional and other changes may be made without departing from the scope of the present invention. The detailed description is, therefore, not to be taken in a limiting sense, and the scope of the present invention is defined by the appended claims.

References within the specification to "one embodiment" or "an embodiment" are intended to indicate that a particular feature, structure, or characteristic described in connection with the embodiment is included in at least one embodiment of the present invention. The appearance of the phrase "in one embodiment" in various places within the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

While the invention has been described in terms of several embodiments, those skilled in the art will recognize that the invention is not limited to the embodiments described, can be practiced with modification and alteration within the spirit and scope of the appended claims. The description is thus to be regarded as illustrative instead of limiting.

What is claimed is:

1. A system for managing medical equipment, the system comprising:
    one or more web servers;
    an equipment tracking module, implemented on the one or more web servers, to maintain equipment records including a plurality of fields corresponding to medical equipment that are shipped from a medical equipment manufacturer to a medical center, wherein the equipment tracking module is configured to allow only the medical equipment manufacturer to create each equipment record about the medical equipment in the equipment tracking module;
    an authentication system, implemented on the one or more web servers, to authenticate a user at the medical center;
    a patient information tracking module, implemented on the one or more web servers, to maintain patient records including a plurality of fields corresponding to patients of the medical center and to associate the patient records with the equipment records when the patients are equipped with the medical equipment, wherein each equipment record is associated with a patient record for a particular patient by way of at least one field and at least one field in the patient record is associated with at least one equipment record; and
    a mapping module, provided through the one or more web servers, to provide locations of medical facilities capable of providing support for the medical equipment for those of the patients that have been discharged from the medical center.

2. The system of claim 1, further comprising:
    a learning management module to present medical equipment training information for the medical center; and
    a product incident module to maintain product incident records to track medical equipment failures.

3. The system of claim 1, wherein the equipment tracking module is to create an equipment record for each medical equipment being shipped when the medical equipment manufacturer initiates a shipment of the medical equipment to the medical center and wherein an initial location of the medical equipment is stored as in transit in the equipment record.

4. The system of claim 3, wherein the equipment tracking module is to add the medical equipment being shipped to an inventory list of the medical center when the medical equipment manufacturer initiates the shipment of the medical equipment to the medical center.

5. The system of claim 1, wherein the medical equipment corresponding to the equipment record that is being associated with the patient record is removed from an inventory list when the equipment record is associated with the patient.

6. The system of claim 2, wherein the mapping module obtains the locations of the medical facilities by using a map database.

7. The system of claim 1, wherein the equipment tracking module is configured to automatically add equipment maintenance reminders to an equipment-to-do list.

8. The system of claim 1, wherein the patient information tracking module is to automatically add patient care reminders and regulatory compliance reminders to a patient-care-to-do list.

9. The system of claim 1, wherein the medical equipment is at least one of an implantable device, an implantable-device-related accessory, a non-implantable device, or a non-implantable-device-related accessory.

10. A computer-implemented method for tracking medical equipment sold by a medical equipment manufacturer, the method comprising:
    generating, by a computer that includes an equipment tracking module, an equipment record including a plurality of fields corresponding to the medical equipment, wherein the equipment tracking module is configured so that the generating of the equipment record is initiated only by the medical equipment manufacturer when the medical equipment manufacturer ships the medical equipment to a medical center, and wherein an initial location of the medical equipment is stored as in transit in the equipment record;
    updating an inventory list of the medical center to include the medical equipment when the equipment record is generated;
    authenticating a user of the medical center based on data received from the user;
    receiving data from the user indicating an association of the equipment record with a patient record including a plurality of fields of a patient when the patient is equipped with the medical equipment, the equipment record associates with a patient record for a particular patient by way of at least one field associated with the patient record and at least one field in the patient record associated with at least one equipment record;
    providing a map which shows locations of medical facilities capable of providing support for the medical equipment for those patients that have been discharged from the medical center; and
    receiving data indicating a disassociation of the equipment record from the patient record when the patient is no longer using the medical equipment.

11. The computer-implemented method of claim 10, further comprising:
    automatically adding equipment maintenance reminders to an equipment-to-do list.

12. The computer-implemented method of claim 10, further comprising:
    automatically adding patient care reminders to a patient-care-to-do list.

13. The computer-implemented method of claim 10, further comprising:
    receiving a user-provided geographic location information corresponding to a target location; and
    providing on the map locations of medical facilities nearby the target location that are capable of providing support for the medical equipment after the patient has been discharged from the medical center.

14. The computer-implemented method of claim 10, wherein the medical equipment is at least one of an implantable device, an implantable-device-related accessory, a non-implantable device, or a non-implantable-device-related accessory.

15. A non-transitory computer-readable storage medium storing instructions thereon, the instructions when executed by a processor causing the processor to perform a method comprising:
    generating, by a computer that includes an equipment tracking module, an equipment record including a plurality of fields corresponding to the medical equipment, wherein the equipment tracking module is configured so that the generating of the equipment record is initiated only by the medical equipment manufacturer when the medical equipment manufacturer ships the medical equipment to a medical center, and wherein an initial location of the medical equipment is stored as in transit in the equipment record;

updating an inventory list of the medical center to include the medical equipment when the equipment record is generated;

authenticating a user of the medical center based on data received from the user;

receiving data from the user indicating an association of the equipment record with a patient record including a plurality of fields of a patient when the patient is equipped with the medical equipment, wherein the equipment record is associated with a patient record for a particular patient by way of at least one field and at least one field in the patient record is associated with at least one equipment record;

providing a map which shows locations of medical facilities capable of providing support for the medical equipment for those patients that have been discharged from the medical center; and receiving data indicating a disassociation of the equipment record from the patient record when the patient is no longer using the medical equipment.

16. The non-transitory computer-readable storage medium of claim 15, wherein the method further comprises:
automatically adding equipment maintenance reminders to an equipment-to-do list.

17. The non-transitory computer-readable storage medium of claim 15, wherein the method further comprises:
receiving a user-provided geographic location information corresponding to a target location; and
providing on the map locations of medical facilities nearby the target location that are capable of providing support for the medical equipment after the patient has been discharged from the medical center.

18. A system for managing medical equipment from a medical equipment manufacturer, the system comprising:
a processor that includes an equipment tracking module; and
a display device coupled to the processor and presenting a graphical user interface (GUI) to a user, wherein the GUI includes a navigation interface element comprising:
an authentication interface to authenticate a user of a medical center;
a patients interface element accessible by the user to display patients lists of the medical center that are associated with the medical equipment;
an equipment interface element coupled to the equipment tracking module and accessible by the user to display an equipment list of the medical center, wherein the equipment tracking module is configured to allow only the medical equipment manufacturer to create an equipment record including a plurality of fields about the medical equipment in the equipment list, the equipment record associated with a patient record for a particular patient by way of at least one field; and
a mapping interface element that is accessible by the user to allow the user to enter locality information to obtain locations, displayed on a map, of medical facilities nearby a target location or along a route of a trip that are capable of providing support for the medical equipment for those patients that have been discharged from the medical center, wherein each patient having a patient record including a plurality of fields and at least one field associated with an equipment record.

19. The system of claim 18, wherein the navigation interface element further comprises:
a to-do interface element accessible by a user to display a patient-care-to-do list and an equipment-to-do list.

20. A method of providing a web portal for use by customers,
including a plurality of medical centers, of a medical equipment provider, the method comprising:
storing equipment information for each medical center, the equipment information being stored in an equipment tracking module accessible through the Internet by each medical center, wherein the equipment tracking module is configured to allow only the medical equipment provider to create an equipment record including a plurality of fields about the medical equipment in the equipment tracking module when the medical equipment provider provides medical equipment to each medical center;
storing patient information, for a plurality of patients, for each medical center, the patient information being stored in a patient module accessible through the Internet by each medical center, each medical center causing entry of data for a particular patient when it associates medical equipment with the particular patient by associating at least one field in the equipment record with the particular patient;
authenticating each medical center when it seeks access to either the patient module or the equipment tracking module;
providing access, through the Internet, to the patient module and to the equipment tracking module to a medical center after authenticating the medical center;
receiving data representing inputs from the medical center, as a result of providing access, and updating at least one of the patient module and the equipment tracking module;
transmitting data to cause the display of a web page at the medical center after receiving and processing the data representing inputs; and
providing a mapping interface that is accessible by a patient to allow the patient to enter locality information to obtain locations, displayed on a map, of medical facilities nearby a target location or along a route of a trip that are capable of providing support for the medical equipment.

21. The method as in claim 20, wherein the patient module and the equipment tracking module are one or more databases controlled by the medical equipment provider, and wherein access to the web portal is controlled by the medical equipment provider, and wherein the equipment information comprises at least one of: (a) product name; (b) identification number; (c) service information; (d) history of ownership of the medical equipment; and (e) To-Do actions, and wherein the patient information comprises at least one of: (a) patient name; (b) contact information; (c) insurance information; (d) reference to equipment information for the patient; and (e) information about equipment servicing.

22. The method as in claim 21, the method further comprising:
transmitting data to cause the display of a user interface (UI) in a web page that allows a user at the medical center to switch between views which include (1) a list of patients having an associated medical equipment; (2) a record for a particular patient; (3) a list of inventory of medical equipment at or used by the medical center; and (4) a summary view showing, for the medical center, a list of patients of the medical center and a list of inventory of medical equipment at or used by the medical center.

23. The method as in claim 22, the method further comprising:
transmitting data to cause the display of a UI in the web page of a view of To-Do maintenance tasks for a medical equipment;
transmitting data to cause the display of a map resource that allows a patient to map out a trip to a medical center; and
transmitting data to cause the display of a product incident report which specifies potential problems with a medical equipment.

24. A machine readable non-transitory storage medium containing executable program instructions which when executed cause a system to perform a method of providing a web portal for use by customers, including a plurality of medical centers, of a medical equipment provider, the method comprising:
storing equipment information for each medical center, the equipment information being stored in an equipment tracking module accessible through the Internet by each medical center, wherein the equipment tracking module is configured to allow only the medical equipment provider to create an equipment record including a plurality of fields about the medical equipment in the equipment tracking module when the medical equipment provider provides medical equipment to each medical center;
strong patient information, for a plurality of patients, for each medical center, the patient information being stored in a patient module accessible through the Internet by each medical center, each medical center causing entry of data for a particular patient when it associates medical equipment with the particular patient by associating at least one field in the equipment record with the particular patient;
authenticating each medical center when it seeks access to either the patient module or the equipment tracking module;
providing access, through the Internet, to the patient module and to the equipment tracking module to a medical center after authenticating the medical center;
receiving data representing inputs from the medical center, as a result of providing access, and updating at least one of the patient module and the equipment tracking module;
transmitting data to cause the display of a web page at the medical center after receiving and processing the data representing inputs; and
providing a mapping interface that is accessible by a patient to allow the patient to enter locality information to obtain locations, displayed on a map, of medical facilities nearby a target location or along a route of a trip that are capable of providing support for the medical equipment.

25. The machine readable non-transitory storage medium as in claim 24, wherein the system is a set of distributed data processing systems that comprise at least one web server and at least one database server coupled to the web server.

26. The machine readable non-transitory storage medium as in claim 24, wherein the method further comprises:
wherein the patient module and the equipment tracking module are one or more databases controlled by the medical equipment provider, and wherein access to the web portal is controlled by the medical equipment provider, and wherein the equipment information comprises at least one of: (a) product name, (b) identification number; (c) service information, (d) history of ownership of the medical equipment; and (e) To-Do actions, and wherein the patient information comprises at least one of: (a) patient name; (b) contact information; (c) insurance information; (d) reference to equipment information for the patient; and (e) information about equipment servicing.

27. The machine readable non-transitory storage medium as in claim 26, wherein the method further comprises:
transmitting data to cause the display of a user interface (UI) in a web page that allows a user at the medical center to switch between views which include (1) a list of patients having an associated medical equipment; (2) a record for a particular patient; (3) a list of inventory of medical equipment at or used by the medical center; and (4) a summary view showing, for the medical center, a list of patients of the medical center and a list of inventory of medical equipment at or used by the medical center.

28. The machine readable non-transitory storage medium as in claim 27, wherein the method further comprises:
transmitting data to cause the display of a UI in the web page of a view of To-do maintenance tasks for a medical equipment;
transmitting data to cause the display of a map resource that allows a patient to map out a trip to a medical center; and
transmitting data to cause the display of a product incident report which specifies potential problems with a medical equipment.

29. A method at a medical center to use a web portal maintained for medical equipment provided by a medical equipment provider, the method comprising:
exchanging data with the web portal to authenticate the medical center with the web portal;
receiving equipment data, from the web portal, about medical equipment provided by the medical equipment provider to the medical center, the equipment data being displayed in a web page on a display device controlled by the medical center, the equipment data being received by a network interface controlled by the medical center, wherein the equipment data is received from an equipment tracking module that includes a database system and wherein the equipment tracking module is configured to allow only the medical equipment provider to create an equipment record including a plurality of fields about the medical equipment in the equipment tracking module;
transmitting patient data, from the medical center to the web portal, for storage in the database system;
displaying a mapping interface that is accessible by a patient to allow the patient to enter locality information to obtain locations, displayed on a map, of medical facilities nearby a target location or along a route of a trip that are capable of providing support for the medical equipment; and
receiving and displaying, at the medical center, patient data and equipment data, the patient data and the equipment data being displayed in a web browser and wherein the web portal provides to the medical center a list of medical equipment from the medical equipment provider that is associated with patients of the medical center and a list of medical equipment in inventory of the medical center, wherein at least one field of the equipment record is associated with a particular patient.

30. The method of claim 29, the method further comprising:
receiving data to cause the display of a user interface (UI) in a web page that allows a user at the medical center to switch between views which include (1) a list of patients having an associated medical equipment; (2) a record for a particular patient; (3) a list of inventory of medical equipment at or used by the medical center; and (4) a summary view showing, for the medical center, a list of patients of the medical center and a list of inventory of medical equipment at or used by the medical center.

31. The method as in claim 30, the method further comprising:
receiving data to cause the display of a UI in the web page of a view of To-Do maintenance tasks for a medical equipment;
receiving data to cause the display of a product incident report which specifies potential problems with a medical equipment; and
wherein the medical equipment comprises an implantable ventricle assist device.

32. The system of claim 1, wherein the medical equipment comprises an implantable ventricle assist device.

33. The computer-implemented method of claim 10, wherein the medical equipment comprises an implantable ventricle assist device.

34. The non-transitory computer-readable storage medium of claim 15, wherein the medical equipment comprises an implantable ventricle assist device.

35. The system of claim 18, wherein the medical equipment comprises an implantable ventricle assist device.

36. The method of claim 20, wherein the medical equipment comprises an implantable ventricle assist device.

* * * * *